(12) United States Patent  
Pacetti et al.

(10) Patent No.: US 9,333,099 B2  
(45) Date of Patent: May 10, 2016

(54) MAGNESIUM ALLOY IMPLANTS WITH CONTROLLED DEGRADATION

(75) Inventors: Stephen D. Pacetti, San Jose, CA (US); Yunbing Wang, Sunnyvale, CA (US); Ni Ding, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 429 days.

(21) Appl. No.: 13/436,538

(22) Filed: Mar. 30, 2012

(65) Prior Publication Data

US 2013/0261735 A1    Oct. 3, 2013

(51) Int. Cl.

| | |
|---|---|
| *A61F 2/82* | (2013.01) |
| *C23C 8/00* | (2006.01) |
| *C23C 8/42* | (2006.01) |
| *C23C 8/80* | (2006.01) |
| *C23C 8/10* | (2006.01) |
| *C23C 26/00* | (2006.01) |
| *C23C 28/04* | (2006.01) |
| *C23C 28/00* | (2006.01) |
| *C23C 30/00* | (2006.01) |
| *A61L 31/02* | (2006.01) |
| *A61L 31/08* | (2006.01) |
| *A61L 31/10* | (2006.01) |

(Continued)

(52) U.S. Cl.
CPC .................. *A61F 2/82* (2013.01); *A61L 31/022* (2013.01); *A61L 31/086* (2013.01); *A61L 31/088* (2013.01); *A61L 31/10* (2013.01); *A61L 31/148* (2013.01); *C23C 8/00* (2013.01); *C23C 8/10* (2013.01); *C23C 8/42* (2013.01); *C23C 8/80* (2013.01); *C23C 26/00* (2013.01); *C23C 28/04* (2013.01); *C23C 28/30* (2013.01); *C23C 30/00* (2013.01); *A61F 2/915* (2013.01); *A61F 2210/0004* (2013.01); *A61F 2250/003* (2013.01); *A61L 2300/416* (2013.01); *A61L 2300/606* (2013.01); *A61L 2400/18* (2013.01)

(58) Field of Classification Search
CPC ............. A61F 2/82; A61F 2/86; A61F 2/915; A61F 2210/0004; A61L 31/022; A61L 31/048
USPC ........................................ 623/1.38; 424/426
See application file for complete search history.

(56) References Cited

U.S. PATENT DOCUMENTS

| | | |
|---|---|---|
| 5,306,286 A | 4/1994 | Stack et al. |
| 5,443,496 A | 8/1995 | Schwartz et al. |
| 5,711,763 A | 1/1998 | Nonami et al. |

(Continued)

FOREIGN PATENT DOCUMENTS

EP            716836            6/1996

OTHER PUBLICATIONS

Zberg et al., MgZnCa glasses without clinically observable hydrogen evolution for biodegradable implants, Nature Materials 8, 887-891 (2009).*

(Continued)

*Primary Examiner* — David Isabella
*Assistant Examiner* — Suba Ganesan
(74) *Attorney, Agent, or Firm* — Squire Patton Boggs (US) LLP

(57) ABSTRACT

Stents or scaffolds made from magnesium or magnesium alloys including additives or barrier coatings that modify the corrosion rate of the stent are disclosed. Methods of forming barrier coatings that modify the corrosion rate of the stent are disclosed.

10 Claims, 2 Drawing Sheets

(51) Int. Cl.
 *A61L 31/14* (2006.01)
 *A61F 2/915* (2013.01)

(56) References Cited

U.S. PATENT DOCUMENTS

| | | | |
|---|---|---|---|
| 6,013,106 | A | 1/2000 | Tweden et al. |
| 6,099,561 | A | 8/2000 | Alt |
| 6,270,831 | B2 | 8/2001 | Kumar et al. |
| 7,011,678 | B2 | 3/2006 | Tenerz et al. |
| 8,172,897 | B2 | 5/2012 | Gale et al. |
| 8,668,732 | B2 * | 3/2014 | Scheuermann et al. ..... 623/1.38 |
| 2003/0219466 | A1 | 11/2003 | Kumta et al. |
| 2004/0241036 | A1 * | 12/2004 | Meyer-Lindenberg et al. .......... 623/23.53 |
| 2005/0163954 | A1 | 7/2005 | Shaw |
| 2005/0209680 | A1 | 9/2005 | Gale et al. |
| 2005/0278015 | A1 | 12/2005 | Dave et al. |
| 2006/0229711 | A1 | 10/2006 | Yan et al. |
| 2007/0135905 | A1 | 6/2007 | Burgermeister et al. |
| 2007/0250158 | A1 | 10/2007 | Krivoruchko et al. |
| 2007/0259101 | A1 | 11/2007 | Kleiner et al. |
| 2007/0288084 | A1 | 12/2007 | Lee et al. |
| 2009/0030500 | A1 * | 1/2009 | Weber et al. ................ 623/1.15 |
| 2009/0088834 | A1 | 4/2009 | Wang |
| 2009/0186068 | A1 | 7/2009 | Miller et al. |
| 2009/0324684 | A1 | 12/2009 | Atanasoska et al. |
| 2010/0076544 | A1 * | 3/2010 | Hoffmann et al. ........... 623/1.15 |
| 2010/0305684 | A1 | 12/2010 | Kim et al. |
| 2011/0022158 | A1 | 1/2011 | Atanasoska et al. |
| 2011/0076319 | A1 * | 3/2011 | Orlowski et al. ............. 424/426 |
| 2011/0118826 | A1 | 5/2011 | Radhakrishnan et al. |
| 2011/0172763 | A1 | 7/2011 | Ndondo-Lay |
| 2011/0307053 | A1 | 12/2011 | Gale et al. |
| 2013/0236498 | A1 * | 9/2013 | Mangiardi .................... 424/400 |

OTHER PUBLICATIONS

Effects of Surface Modification on Biocompatibility of Magnesium Alloy AZ811, posted in Home www.medical-science.net, 1 pg. downloaded Jul. 31, 2012.

Erbel et al., "Temporary scaffolding of coronary arteries with bioabsorbable magnesium stents: a prospective, non-randomised multicenter trial", www.thelancent.com vol. 369 Jun. 2, 2007, pp. 1869-1875.

Heublein et al., "Biocorrosion of magnesium alloys: a new principle in cardiovascular implant technology?", Heart 89, pp. 651-656 (2003).

Valenzuela et al., "Variability of water uptake studies of biomedical polymers", J. of Applied Polymer Science vol. 121, iss. 3, pp. 1311-1320 (2011) Abstract, 3 pgs.

Waksman et al., "Safety and efficacy of bioabsorbable magnesium alloy stents in porcine coronary arteries", Catheterization and Cardiovascular Interventions 68, pp. 607-617 (2006).

Wang "Hydroxyapatite degradation and biocompatibility", dissertation, Ohio State Univ. Abstract 4 pgs. (2004).

* cited by examiner

MAGNESIUM ALLOY IMPLANTS WITH CONTROLLED DEGRADATION

BACKGROUND OF THE INVENTION

1. Field of the Invention

This invention relates to implantable medical devices, in particular stents, fabricated from corrodible metals.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel, or other anatomical lumen, such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, to a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as hoop or circumferential strength and rigidity.

Once expanded, the stent must adequately maintain its size and shape throughout its service life despite the various forces that may come to bear on it, including the cyclic loading induced by pulsatile blood flow. For example, a radially directed force may tend to cause a stent to recoil inward. Generally, it is desirable to minimize recoil. In addition, the stent must possess sufficient deformational capability to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts, links, crests, or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Coronary stents made from non-erodible metals have become the standard of care for percutaneous coronary intervention (PCI) since such stents have been shown to be capable of preventing early and later recoil and restenosis. Despite the positive success of such stents in PCI, a drawback of such durably implanted stents is that the permanent interaction between the stent and surrounding tissue can pose a risk of endothelial dysfunction and late thrombosis.

Thus, it may be desirable for a stent to be biodegradable or bioerodible. In the treatment of coronary heart disease with a stent, the presence of the stent in a body is necessary for a limited period of time until its intended function of, for example, maintaining vascular patency and/or drug delivery. Therefore, there is a need to address issues relating to the erosion of a stent made from bioerodable materials such as bioerodable metals that eventually completely erode after the clinical need for them has ended.

SUMMARY OF THE INVENTION

Various embodiment of the present invention include a stent comprising a scaffold composed of a homogeneous or heterogeneous alloy(s) comprising a magnesium content of 30 to 80 wt % and a zinc or iron content of 10 to 70 wt %.

Various embodiment of the present invention include a stent comprising a scaffold composed of plurality of struts, wherein the struts comprise: a shell composed of a first erodible metal; and a core composed of a second erodible metal surrounded by the shell, wherein the first erodible metal is slower eroding than the second erodible metal, wherein the first erodible metal comprises zinc or iron, wherein the second erodible metal is a magnesium alloy.

A stent comprising a scaffold composed of plurality of struts, wherein the struts comprise: an abluminal layer and a luminal layer composed of a first erodible metal; and a middle layer composed of a second erodible metal between the abluminal and luminal layers, wherein the first erodible metal is slower eroding than the second erodible metal, wherein the first erodible metal comprises zinc or iron, wherein the second erodible metal is a magnesium alloy.

Various embodiment of the present invention include a stent comprising: a scaffold composed of a magnesium alloy; and a coating layer above the scaffold surface, wherein the coating is composed of an erodible metal that is slower eroding than the magnesium alloy of the scaffold, wherein the slower eroding metal is selected from the group consisting of iron, iron alloy, zinc, and zinc alloy, wherein a thickness of the coating layer is between 0.1 and 10 microns.

Various embodiment of the present invention include a stent comprising: a scaffold composed of a magnesium alloy; and a coating layer above the scaffold surface, wherein the coating is composed of a biodegradable polymer, wherein the number average molecular weight (Mn) of the polymer is greater than 500 kDa.

Various embodiment of the present invention include a stent comprising: a scaffold composed at least in part of a mixture of a magnesium alloy and a plurality of elemental calcium particles, wherein the plurality of elemental calcium particles are dispersed within the magnesium alloy, and wherein the particles have a size between 0.1 and 10 microns and are between 5 and 25 wt % of the mixture.

Various embodiment of the present invention include a stent comprising: a scaffold composed at least in part of a mixture of a magnesium alloy and a plurality of particles, wherein the plurality of particles is dispersed within the magnesium alloy, wherein the particles include a first type of particles and a second type of particles, wherein the first type is particles of an inorganic salt of calcium other than calcium phosphate and the second type is particles of an inorganic salt of phosphate or carbonate other than calcium phosphate or calcium carbonate, wherein the particles have a size between 0.1 and 5 microns and are between 5 and 25 wt % of the mixture.

Various embodiment of the present invention include a stent comprising: a scaffold composed of a magnesium alloy; and a coating above the scaffold surface, wherein the coating comprises a bioglass layer composed of bioglass, wherein the bioglass layer is nonporous and is 0.1 to 2 microns in thickness, wherein the coating comprises a second layer above the bioglass layer composed of a polymer and a drug.

Various embodiment of the present invention include a stent comprising: a scaffold composed of a magnesium alloy; and a coating above the scaffold surface, wherein the coating comprises a hydroxyapatite layer composed of hydroxyapatite, wherein the hydroxyapatite layer is 0.05 to 25 microns in thickness.

Various embodiment of the present invention include a method of fabricating a stent comprising: providing a scaffold composed of a magnesium alloy; processing the scaffold to oxidize a surface of the scaffold which forms a layer comprising magnesium oxide; and performing a hydrolysis step to convert the magnesium oxide to magnesium hydroxide; wherein a thickness of the layer is between 0.1 and 10 microns.

Various embodiment of the present invention include a stent comprising: a scaffold composed of a magnesium alloy; and a coating above the scaffold surface, wherein the coating is composed of a magnesium salt of phosphate or ammonium phosphate, wherein the coating has a thickness between 0.1 and 10 microns.

Various embodiment of the present invention include a method of fabricating a stent comprising: providing a scaffold composed of a magnesium alloy; exposing a surface of the scaffold to a solution including ammonium or phosphate ions in the presence of a mineral acid comprising HCl, $H_3PO_4$, $HClO_4$ or $H_2SO_4$ to oxidize magnesium on the surface and precipitate a magnesium phosphate or magnesium ammonium phosphate salt layer on the surface, wherein a thickness of the layer is between 0.1 and 10 microns.

Various embodiment of the present invention include a method of fabricating a stent comprising: providing a scaffold composed of a magnesium alloy; exposing a surface of the scaffold to a solution including ammonium or phosphate ions in the presence of an oxidizing agent to oxidize magnesium on the surface of the scaffold, wherein a thickness of the layer is between 0.1 and 10 microns.

DETAILED DESCRIPTION OF THE INVENTION

Various embodiments of the present invention relate to stents made from magnesium or magnesium alloys that include additives or barrier coatings that modify the corrosion rate of the stent. These embodiments are applicable to, but are not limited to, self-expandable stents, balloon-expandable stents, stent-grafts, and generally tubular medical devices.

Figure 1:
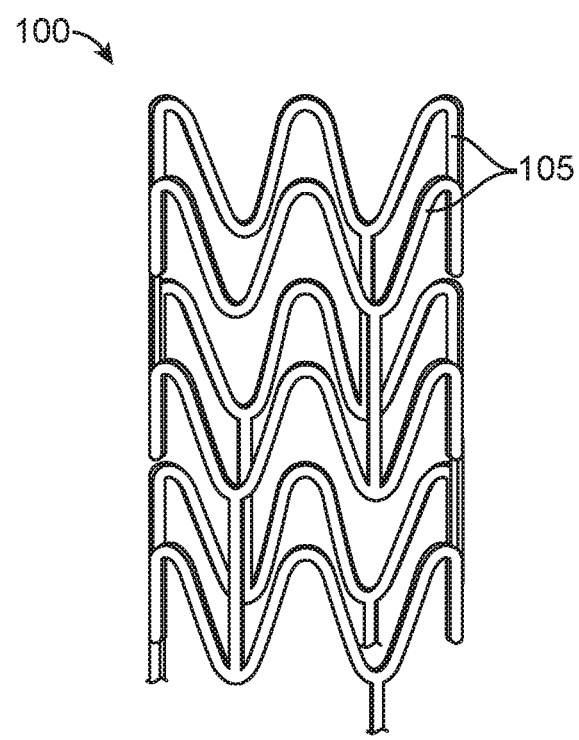
FIG. 1 depicts a view of a stent.

A stent may include a pattern or network of interconnecting structural elements or struts. FIG. 1 depicts a view of a stent 100. In some embodiments, a stent may include a body, backbone, or scaffolding having a pattern or network of interconnecting structural elements 105. Stent 100 may be formed from a tube (not shown). The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited.

A stent such as stent 100 may be fabricated from a metallic tube or a sheet by rolling and bonding the sheet to form the tube. A tube or sheet can be formed by drawing, extrusion or casting. A stent pattern, such as the one pictured in FIG. 1, can be formed in a tube or sheet with a technique such as laser cutting or chemical etching. The stent can then be crimped on to a balloon or catheter for delivery into a bodily lumen.

The embodiments of the stents of the present invention can be designed for the localized delivery of a therapeutic agent. A medicated stent may be constructed by coating the substrate or scaffold with a coating material containing a therapeutic agent. The substrate of the device may also contain a therapeutic agent.

While stents have typically been constructed of relatively inert metals in order to ensure their longevity, degradable or erodible stent structures have more recently been devised in an effort to provide support for only a limited period of time. In general, the support or patency provided by a stent for the treatment of a stenosis is required only for a limited period of time. For example, a preferred or required treatment time by a stent may be less than 18 months, less than a year, between three and 12 months, or more narrowly, between four and eight months.

Once the stent, erodible or nonerodible, is deployed in vessel, the stent is required to maintain patency of the vessel which corresponds to supporting the vessel at or close to the deployed diameter for a period of time to allow for remodeling of the vessel wall. To accomplish this, the stent should be capable of applying an outward radial force to counter the inward radial force imposed by the vessel wall, including the cyclic loading induced by the beating heart. In the case of an erodible stent, the stent should maintain such patency in spite of the degradation or erosion of the stent body for a period of time. Thus, the stent should have sufficient strength, stiffness (modulus) to maintain patency of the vessel wall.

Furthermore, the stent should be sufficiently tough to resist failure or fracture of the structural elements of a stent. One measure of toughness is the area under a stress-strain or load elongation curve from zero strain to the strain at fracture. Therefore, the modulus, stress at failure (strength), and elongation at failure are relevant to the toughness of a metal or alloy. The bending regions of a typical stent structure are the most susceptible to failure during use. Therefore, an erodible stent structure should have the appropriate combination of mechanical properties and degradation or erosion properties to provide patency during a specified treatment period.

The terms degrade, absorb, erode, as well as degraded, absorbed, eroded, are used interchangeably and refer to materials that are capable of being completely eroded, or absorbed when exposed to bodily conditions. Such materials may be capable of being gradually resorbed, absorbed, and/or eliminated by the body.

"Corrosion" generally refers to the deterioration of essential properties in a metal due to reactions with its surroundings. Corrosion of a metal can occur upon contact with a variety of materials including air, water, organic solvents, etc. As it is used herein, corrosion refers to deterioration or degradation of a metal due to contact with water, such as bodily fluids containing water in a vascular environment. The degradation can result in deterioration of mechanical properties of a metallic construct and mass loss from the construct.

Corrosion in an environment that contains moisture involves a series of reactions that first result in the formation of metal ions, and secondly lead to removal of metal atoms from the metal surface. Corrosion resulting from contact with bodily fluids containing water results in oxidation of the metal (loss of electron(s)) as the metal reacts with water and oxygen. The metal atoms at the surface lose electrons and become positively charged ions that leave the metal to form salts in solution. Corrosion reactions generally involve both oxidation and reduction reactions. The metal is oxidized with subsequent reduction of hydrogen ions and oxygen in solution. The reduction reactions drive the oxidation reactions.

Many erodible metals and metal alloys, such as magnesium, iron, zinc, tungsten, and their alloys, may be promising as stent materials. However, these and other metals may not provide a desired combination of degradation and mechanical behavior for a stent during a desired treatment period. In particular, certain metals, such as magnesium, may degrade too quickly, exhibiting a corrosion that is faster than is desired. Specifically, as the stent corrodes the radial strength, as well as other mechanical properties, decreases. Eventually the stent reaches radial strength that can no longer maintain patency. Therefore, metals that corrode too fast may not provide radial strength that maintains patency for a period of time required for remodeling of the vessel wall.

An exemplary desired degree of patency is no less than 50% of the deployed diameter of the stent. It is believed that radial strength should be maintained for at least 3 months after implantation to achieve the desired degree of stabilization and remodeling of the vessel wall. A late lumen loss that is higher than desired demonstrated in a clinical setting may be indicative that radial strength is not maintained for a sufficient period of time.

Heublein et al. conducted a series of in vitro and in vivo preclinical trials using stents made of magnesium alloy. Heublein, B. et al. Heart 2003; 89:651-656. These studies demonstrated relatively high rates of degradation from 60 to 90 days, with loss of mechanical integrity at between 36 and 56 days after implantation and complete stent degradation estimated at 89 days. Heublein, B. et al. Heart 2003; 89:651-656 A clinical study initiated in 2005 using a magnesium alloy stent showed after four months a late lumen loss of 0.83 mm and also that stent struts were not visible, indicating complete degradation of the scaffold. Erbel, R. et al., Lancet vol. 369, Jun. 2, 2007.

Another generation of magnesium alloy scaffolds has been developed by the same company as the stent that was the subject of the trials described in Erbel et al. This stent is described as having a refined alloy that erodes slower than that of the previous generation stent. The clinical results reported for this second trial showed that the late loss at 6 months was as high as 0.68 mm. This level of late loss for this magnesium alloy stent suggests a premature loss of mechanical support of scaffold. One way to address this premature loss is a reduction in the corrosion rate of the scaffold.

Thus, approaches are needed for adjusting, controlling, modifying, or tailoring the in vivo erosion rates and mechanical properties of erodible metallic stents, in particular stents made of magnesium alloys. It is desirable to adjust the erosion rate of the stent without unacceptably compromising properties such as radial strength or biocompatibility.

A stent body, scaffolding, or substrate can refer to a stent structure with an outer surface to which no coating or layer of material different from that of which the structure is manufactured. If the body is manufactured by a coating process, the stent body can refer to a state prior to application of additional coating layers of different material. By "outer surface" is meant any surface however spatially oriented that is in contact with bodily tissue or fluids. A stent body, scaffolding, or substrate can refer to a stent structure formed by laser cutting a pattern into a tube or a sheet that has been rolled into a cylindrical shape.

Some embodiments of controlling the corrosion rate of erodible metal stents can include an alloy that includes magnesium or a magnesium alloy mixed with slower eroding metals. Such slower eroding metals include iron or zinc. The alloys of the present invention can include at least 10% elemental zinc or iron.

In exemplary embodiments, the magnesium alloys can be between 10 and 70 wt %, 10 to 20 wt %, 20 to 30 wt %, 30 to 40 wt %, 40 to 50 wt %, and 50 to 70 wt % elemental iron or zinc content. The alloy can include 30 to 90 wt % magnesium, or more narrowly, 30 to 40 wt %, 40 to 50 wt %, 50 to 70 wt %, or 70 to 90 wt % magnesium. The alloys can include lesser percentages of other metals (e.g., less 10%) such as aluminum, gallium, zirconium, manganese, silicon, bismuth, and neodymium. The alloys can be free of any of the metals disclosed herein, other than magnesium. The alloys may be nonporous, porous, drug-free, or contain a drug. The alloys can have 0.1 to 1%, 1 to 2%, 1 to 5%, 2 to 5%, less than 1%, less than 2%, or less than 5% porosity. Porosity is defined as the ratio of void volume to total volume of a material and the total volume does include the volume of gaps in between structural elements of a stent structure. The scaffold may be formed completely of the alloys.

In these embodiments, the magnesium alloys can be a complete solid solution or a partial solid solution, resulting in homogeneous alloy with a single phase. Alternatively, the magnesium alloys can be heterogeneous alloys containing multiple phases with interstitial structure as an example. The multiple phases can include a phase composed of magnesium or magnesium alloy having up to 5 wt % of iron or zinc or 1 to 5 wt % of iron or zinc. The multiple phases can include a phase composed primarily or completely of zinc or iron.

The alloys with high content of iron or zinc can be prepared by melting and mixing magnesium or magnesium alloy, iron or zinc and other elements, for example in a vacuum induction furnace under argon atmosphere. Tubing can be formed from the resulting ingot and a scaffold may be obtained from mixture tubing by laser cutting the tube.

In further embodiments, an erodible metal stent can include a scaffold composed of struts having a structure that includes a core and an outer shell. The shell is composed of a metal that is slower eroding than the core. The core is made of a magnesium alloy and the shell is composed of a metal that is slower eroding than the core magnesium or magnesium alloy.

The slower eroding metal can include iron, iron-magnesium alloy, iron alloy, zinc, zinc magnesium alloy, and zinc alloy. A ratio of a thickness of the core to the shell may be between 10:1 and 2:1. The thickness of the shell can be 2 to 50 microns.

Figure 2A:
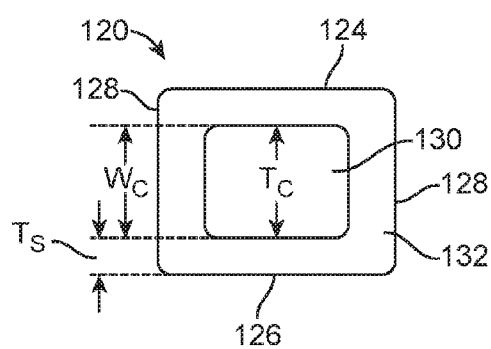
FIG. 2A depicts a cross-section of a strut of a stent with a core and a shell surrounding the core.
Figure 2B:
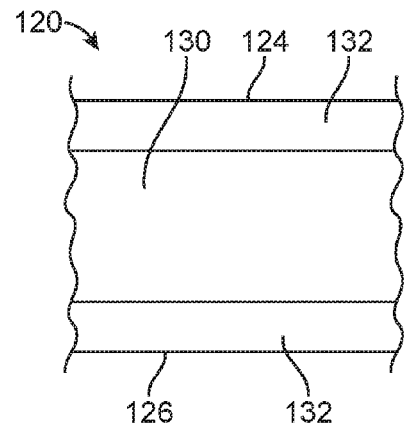
FIG. 2B depicts an axial cross-section of the strut depicted in FIG. 2A.

FIG. 2A depicts a cross-section of a strut 120. FIG. 2B depicts an axial cross-section of strut 120. Strut 120 has a luminal surface 124 and an abluminal surface 126 and a side wall surfaces 128. Strut 120 has a core 130 surrounded by an outer shell 132. Core 130 has a thickness in the radial direction Tc and shell 132 has a thickness Ts. Core 130 has a width We that may be different from Tc if the strut is not square in cross section.

A scaffold composed of struts with a core and shell of different metals may be made by making the struts separately and welding them together into a scaffold pattern. Alternatively, a tube made of the core metal material may be laser machined to form the scaffold pattern. The scaffold pattern then may be coated with the shell metal material using various methods such as plasma deposition, electroplating, sputter coating, or vacuum evaporation.

In another methodology, a core and shell strut is formed by drawing wire composed of a core and a shell. The resulting wire can have any cross-sectional shape including square, rectangular, round, or oval. This wire is then fabricated into a stent by cutting the wire into segments, forming the segments into rings and welding them closed, stamping crests into the rings, and welding the rings together at selected points to form a stent. Otherwise, the wire may be formed into a continuous sinusoid, this sinusoid is wrapped around a mandrel to form a helix, and the rows of the helix welded to together at selected points to form a stent.

In other embodiments, the struts of a scaffold of a stent can include an abluminal layer, a luminal layer, and a middle layer between the abluminal and luminal layers. The middle layer is magnesium or a magnesium alloy. The abluminal and luminal layers are composed of a metal that is slower eroding than the middle layer of magnesium or magnesium alloy. The abluminal and luminal layers may have the same composition or may have different composition. A ratio of a thickness of the core to a luminal or abluminal layer may be between 20:1 and 4:1. The thickness a luminal or abluminal layer can be 2 to 30 microns, or more narrowly, 10 to 20 microns, or 20 to 30 microns.

Figure 3A:
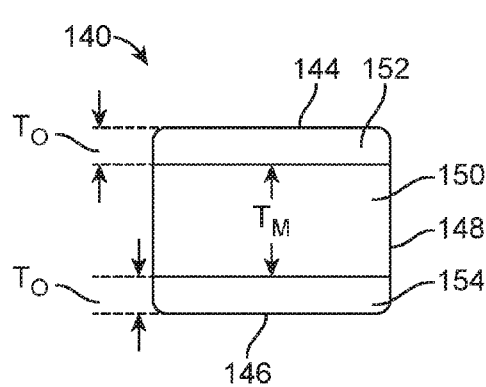
FIG. 3 depicts a section of a strut of a stent having an abluminal layer, luminal layer, and a middle layer.
Figure 3B:
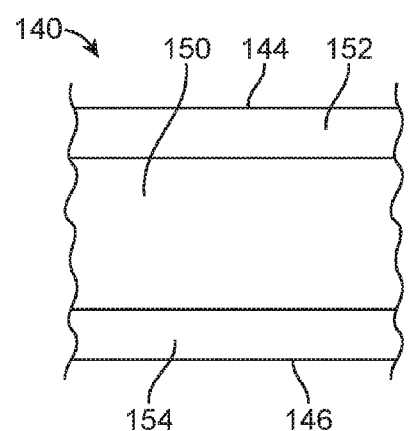

FIG. 3A depicts a cross-section of a strut 140. FIG. 3B depicts an axial cross-section of strut 140. Strut 140 has a luminal surface 144 and an abluminal surface 146 and a side wall surface 148. Strut 140 has a middle layer 150 which is between a luminal layer 152 and an abluminal layer 154. Middle layer 150 has a thickness Tm and luminal layer 152 and abluminal layer 154 have a thickness To.

The three-layer tube with magnesium alloy in the middle and the slow eroding metals layers can be manufactured by co-extrusion. Such a tube drawing process could be applied with a magnesium alloy as the inner layer. The extruded tubing may then be machined to form a scaffold. Alternatively, the three layer scaffold can be made from three concentric tubes. The inner and outer tubes are made of the slow eroding metal and the middle tube is made of the magnesium alloy. Additionally, to cover the exposed side walls, the three layer scaffold can be coated with a slow eroding metal.

The core or middle layer of the two sets of embodiments above can be made from pure magnesium or a magnesium single phase or multi-phase alloy with a magnesium content of 30 to 99 wt %, or more narrowly, 50 to 90 wt %, 60 to 90 wt %, or 70 to 90 wt %. The middle layer can have zinc or iron content of 10 to 70 wt %.

The slow eroding metal of the shell or abluminal/luminal layers may be pure zinc or pure iron. The slow eroding metal can be a single phase or multi-phase alloy including 10 to 100 wt % of iron or zinc, or more narrowly 10 to 70 wt %, 10 to 20 wt %, 20 to 40 wt %, 40 to 60 wt %, 60 to 80 wt % zinc or iron content.

Upon implantation of the stent embodiments described, the slow eroding shell or abluminal/luminal layers prevent, reduce, inhibit exposure of the core or middle layer to bodily fluids so that erosion of the core is delayed. Therefore, the shell or outer layers slow the erosion rate and the degradation of mechanical properties, such as radial strength.

In further embodiments, an erodible metal scaffold composed of magnesium or magnesium alloy can have a thin slower erodible metal coating over all or some of the scaffold as a moisture barrier to delay erosion of the scaffold. The slower eroding metal of the coating includes iron, iron alloy, zinc, or zinc alloy.

The slower eroding metal may have a thickness of 0.01 to 10 microns, or more narrowly, 0.1 to 5, 1 to 5 microns, about 1 micron, about 2 microns, or about 3 microns. The slow eroding metal layer may be all or mostly elemental metal(s). The slow eroding metal layer may be free of metal oxides or may have less then 1 wt %, 2 wt %, or less than 5 wt % oxides. The slow eroding metal layer may be free of metal compounds other than oxides or may have less then 1 wt %, 2 wt %, or less than 5 wt % other metal compounds other than oxides. The slower eroding metal layer may be nonporous or have less than 1%, less than 2%, or less than 5% porosity.

Methods of coating the magnesium alloy scaffold with the slow eroding metal include electroplating, electroless deposition, chemical vapor deposition, sputter coating, and vacuum evaporation techniques.

The slow eroding metal of the shell or abluminal/luminal layers may be pure zinc or pure iron. The slow eroding metal can be an alloy including 10 to 100 wt % of iron or zinc, or more narrowly 10 to 70 wt %, 10 to 20 wt %, 20 to 40 wt %, 40 to 60 wt %, 60 to 80 wt % zinc or iron content.

In another embodiment, a barrier layer over magnesium or magnesium alloy scaffold includes a biodegradable polymer. The polymer can have a molecular weight 10 to 100 kDa, 50 to 70 kDA, 60 to 100 kDa, 100 to 150 kDa, 100 to 200 kDa, greater than 10 KDa, 300 kDa, 400 kDa, 500 kDa, 700 kDa, or greater than 1000 kDa. The molecular weight may refer to either number average molecular weight or weight average molecular weight.

The biodegradable polymer may be a semicrystalline polymer. The biodegradable polymer may also be a bulk-eroding semicrystalline polymer.

A bulk-eroding polymer refers to a polymer that degrades in the bulk of the polymer below a moisture contacting surface. Water can penetrate into a bulk eroding polymer before moisture-contacting surface regions erode away from the polymer. This allows chemical degradation (e.g., chain scission due to hydrolysis) of the polymer to occur throughout most or the entire polymer prior to complete erosion of the polymer. Therefore, the bulk eroding polymer may allow some contact of moisture with the metal scaffold surface prior to disappearance of the barrier layer.

The biodegradable polymer may contain a drug or may be drug-free. The polymer layer may be nonporous or may have a porosity of 1 to 5%, less than 1% or less than 5%.

The biodegradable polymer coating with and without crystallinity has water absorption less than 5%, less than 2%, preferable less than 1% before implant.

The polymer layer may be disposed over the scaffold body by various techniques including spray coating, dip coating, or roll coating. The thickness of the layer can be from 0.2 up to 10 microns, or more narrowly, 1 to 5 microns, 2 to 3 microns, about 3 microns, or about 2 microns.

After the deposition of a semicrystalline polymer on a magnesium alloy scaffold, the coating layer may be annealed to increase the crystallinity. The increased crystallinity increases the resistance of water or moisture penetration. The crystallinity of the polymer layer may be greater than 20%, 30%, 40%, 50%, or 60%. The crystallinity of the polymer layer may be 20 to 60%, 30 to 60%, 40 to 50%, 50 to 60%, 30 to 50%, or 40 to 50%.

The polymer of the biodegradable layer may be a biodegradable aliphatic polyester. The non-exclusive examples of biodegradable polymers can include poly(L-lactide), poly(D-lactide), poly(D,L-lactide), polyglycolide, polycaprolactone, poly(trimethylene carbonate), poly(hydroxyl alkanoate), poly(butylene succinate). Additional biodegradable polymers include L-tyrosine-derived polyarylates such as poly (HTH sebacate), poly(DTO sebacate), poly(DTO succinate), poly(DTB succinate), poly(DTO adipate), poly(HTE adipate), poly(DTH suberate), poly(DTM sebacate), poly(DTM adipate), poly(DTB glutarate), poly(HTH adipate), poly(DTH adipate), poly(DTB adipate), poly(DTsB sebacate), and poly(DTE glutarate).

Biodegradable polymers with a low water uptake are preferred to delay corrosion of the magnesium or magnesium alloy scaffold. The water uptake of biodegradable polymers has been studied by Valenzuela et al. J. of Appl. Pol. Sci., Vol. 121, 1311-1320 (2011). The polymer may have a percent water uptake of 1 to 5 wt %, 1 to 10 wt %, 5 to 10 wt %, 5 to 20 wt %, 10 to 20 wt %, less than 5 wt %, less than 10 wt %, or less than 20 wt %. The water uptake can refer to in vitro equilibration in aqueous solutions or in vivo, or water uptake in such conditions at least up to 28 days or 3 months. The molecular weight, weight or number average, can be selected to have the selected water uptake.

Further embodiments of the present invention include a magnesium or magnesium alloy scaffold that includes particulate additives that control, modify, or adjust the erosion rate of the scaffold. Such particulate additives may be dispersed in part or all of the metal of the scaffold. The particles can be dispersed uniformly or homogeneously throughout the scaffold or a region of the scaffold. The additives may reduce the corrosion rate of the metal of magnesium or magnesium alloy of the scaffold. Particulate additives do not refer to elements or compounds mixed in a metal or alloy on an atomic or molecular level. The size of the particles may be from 0.01 to 0.1 micron, 0.1 to 10 microns, 0.1 to 1 micron, 1 to 3 microns, 0.1 to 5 microns, 1 to 5 microns, or 1 to 10 microns.

In some embodiments, particulate additives include particles of calcium metal dispersed with the magnesium or magnesium alloy of a scaffold. The calcium particle content may be 0.5 to 25 wt %, or more narrowly 0.5 to 10 wt %, 1 to 10 wt %, 1 to 5 wt %, 5 to 10 wt %, or 10 to 20 wt % of the scaffold, the alloy-particle mixture, or a portion of the scaffold. The metal of the scaffold may be free of calcium compounds other than elemental calcium or may have less than 1 wt %, 2 wt %, or less than 5 wt % of such compounds.

In some embodiments, the entire scaffold can be made of the alloy-particle mixture. In other embodiments, a portion of the scaffold can be made of the alloy-particle mixture. In one embodiment, the scaffold structure can include a core of magnesium alloy with a shell composed of the alloy-particle mixture, as depicted in FIG. 2. The core can be free of the calcium particles. The above-mentioned dimensions for the core and shell apply this embodiment.

Alternatively, the scaffold structure can include luminal and abluminal layers composed of the alloy-particle mixture and a middle layer between these layers, as depicted in FIG. 3. The middle layer can be free of the calcium particles.

In another embodiment, a magnesium alloy scaffold that may be free of the calcium particles and can include an alloy-calcium particle mixture coating over all or part of the scaffold. Such a coating may have a thickness of 1 to 5 microns, 1 to 10 microns, or 5 to 10 microns.

When a scaffold including an alloy-calcium particles mixture is implanted, the scaffold is exposed to bodily fluids and degrades and the metallic calcium in the alloy is converted quickly to $Ca^{2+}$ ions at the particle-fluid interface. Calcium is more electropositive than magnesium and will preferentially be oxidized when exposed to water and oxygen. In doing so, the calcium will protect the magnesium from oxidation. The particles may also be released.

Bodily fluids, such as blood, are saturated or nearly saturated with calcium. The larger calcium concentration at the alloy or particle surface will cause precipitation of calcium phosphate and calcium carbonate salts. These salts, which include calcium phosphate ($Ca_2PO_4$), hydroxyapatite ($Ca_{10}(PO_4)_6(OH)_2$), and calcium carbonate ($CaCO_3$) will form an insoluble or low solubility layer on the surface of the alloy, slowing its degradation.

Calcium has a melting point of 839 deg C. versus magnesium at 650 deg C. Thus, calcium particles may be dispersed in magnesium or magnesium alloy through melt processing, such as tube extrusion. The scaffold can then be laser machined from the tube.

Further particulate additives for controlling erosion of a magnesium or magnesium alloy scaffold can include particles of inorganic salts. The particles can include inorganic salts of calcium, inorganic salts of phosphate, and inorganic salts of carbonate. The scaffold can include combinations of any of the above.

The scaffold can include particle combinations of calcium salts other than calcium phosphate and phosphate salts other than calcium phosphate. The scaffold can include particle combinations of calcium salts other than with calcium phosphate and carbonate salts other than with calcium.

Exemplary calcium salts include $CaCl_2$, $CaBr_2$, $Ca(OH)_2$, $CaSO_4$. Exemplary phosphate salts include $Na_3PO_4$, $Na_2HPO_4$, $NaH_2PO_4$, $K_3PO_4$, $K_2HPO_4$, $KH_2PO_4$, and $Mg_3(PO_4)_2$. Exemplary carbonate salts include $CaCO_3$, $NaHCO_3$, $Na_2CO_3$, $KHCO_3$, $K_2CO_3$, $LiHCO_3$, $CaMg(CO_3)_2$, and $Li_2CO_3$.

In a manner similar to the calcium particle embodiments, the entire scaffold can be made of the alloy-particle mixture, the scaffold structure can include a core of magnesium alloy with a shell composed of the alloy-particle mixture, or the scaffold structure can include luminal and abluminal layers composed of the alloy-particle mixture and a middle layer between these layers.

The inorganic particle content may be 0.5 to 25 wt %, or more narrowly 0.5 to 10 wt %, 1 to 10 wt %, 1 to 5 wt %, 5 to 10 wt %, or 10 to 20 wt % of the scaffold, the alloy-particle mixture, or a portion of the scaffold. The metal of the scaffold may be free of one or more of the salts disclosed herein or may have less than 1 wt %, 2 wt %, or less than 5 wt % of such compounds.

Particles of the inorganic salts may be added to a magnesium alloy during melt processing of the alloy. Thus, the inorganic salt particles may be dispersed in a magnesium or magnesium alloy through melt processing, such as tube extrusion. The scaffold can then be laser machined from the tube.

In further embodiments, a magnesium or magnesium alloy scaffold can include a bioglass layer over the scaffold as a moisture barrier. Bioglass refers to bioresorbable glass ceramics composed of $SiO_2$, $Na_2O$, $CaO$, and $P_2O_5$ in specific proportions. Commercially available glass ceramics include Bioglass® derived from certain compositions of $SiO_2$—$Na_2O$—$K_2O$—$CaO$—$MgO$—$P_2O_5$ systems. Some commercially available glass ceramics include, but are not limited to:

45S5: 46.1 mol % $SiO_2$, 26.9 mol % $CaO$, 24.4 mol % $Na_2O$ and 2.5 mol % $P_2O_5$;

58S: 60 mol % $SiO_2$, 36 mol % $CaO$, and 4 mol % $P_2O_5$; and

S70C30: 70 mol % $SiO_2$, 30 mol % $CaO$.

The bioglass coatings can be above or over all or a portion of the magnesium or magnesium alloy scaffold. The thickness of the bioglass coating can be less than 5 microns, less than 2 microns, or less than 1 micron. The thickness of the bioglass coating can be 0.1 to 5 microns, 0.1 to 2 microns, 1 to 2 microns, 1 to 3 microns, about 2 microns, or about 3 microns. A relatively thin coating is preferable since a thinner coating of bioglass can be flexible, rather than brittle. Thus, the coating may be sufficiently thin that cracking is reduced or eliminated during use such as when the stent is crimped or expanded to a deployed configuration.

The bioglass coating may be nonporous or have a porosity less than 1%, less than 2%, or less than 5% porosity. The bioglass layer may also be free of drugs or therapeutic agents. The bioglass layer may also be free of particulates. The bioglass material of the bioglass layer may also be in non-particulate form.

Another embodiment of a protective coating on the magnesium alloy scaffold is addition of a hydroxyapatite coating over the scaffold. The protection is dependent on the thickness of hydroxyapatite (HA) layer. The HA coating can be applied via dip coating of HA fine powder slurry (followed by high temperature sintering), sputter coating, pulse laser deposition, an electrophoretic deposition (followed by sintering), plasma spraying, thermal spraying and sol-gel process. The thickness of a HA coating layer may be from 0.05 to 25 microns, or more narrowly, from 5 to 10 microns and is dependent on the application method. The HA coating layer may be nonporous or porous. The coating layer can have 0.1 to 1%, 1 to 2%, 1 to 5%, 2 to 5%, less than 1%, less than 2%, or less than 5% porosity. The coating layer may be drug-free or contain a drug.

Further embodiments of a barrier layer over a magnesium or magnesium alloy scaffold includes a layer including or composed of magnesium oxide, magnesium hydroxide, or both. An oxide layer can be formed on a scaffold using various methods including electro-chemical, plasma, micro-arc oxidation, ozone treatment, corona discharge, and alkaline solution treatment.

In an electro-chemical treatment, the magnesium alloy acts as the anode, resulting in oxidation of a surface layer of the scaffold. Plasma treatment refers to the treatment of materials with low-temperature plasmas generated in arc or high-frequency plasmatrons. Plasma is any substance (usually a gas) whose atoms have one or more electrons detached and therefore become ionized. The detached electrons remain, however, in the gas volume that in an overall sense remains electrically neutral. Thus, any ionized gas that is composed of nearly equal numbers of negative and positive ions is called plasma.

Corona discharge treatment refers to a surface modification technique that uses a low temperature corona discharge plasma to impart changes in the properties of a surface. The corona plasma is generated by the application of high voltage to sharp electrode tips which forms plasma at the ends of the sharp tips. A linear array of electrodes is often used to create a curtain of corona plasma.

The oxidation step can form a layer that includes compounds such as $Mg(OH)_2$, $MgO$, or $Mg$—$O_n$—$X$ (where X is some other metal such as Zn, Al, Si, etc.). The compounds formed depend on the conditions, and the presence of water in the process. Temperatures above 340° C. favor the formation of magnesium oxide, while temperature below this allow for the formation of the less water soluble magnesium hydroxide. The thickness of the oxide layer can be 0.1 to 10 microns, or more narrowly, 0.1 to 5 microns, 1 to 5 microns, 2 to 3 microns, about 2 microns, or about 3 microns.

The plasma treatment can include oxygen, air, or water plasma treatment. The corona discharge treatment may be at atmospheric pressure. The alkaline solution treatment may be performed with sodium hydroxide, potassium hydroxide, trisodium phosphate, ammonium hydroxide, sodium carbonate, sodium bicarbonate, sodium borate, magnesium carbonate, and the mixtures thereof.

The scaffold may further be treated with a hydrolysis step to convert surface MgO to $Mg(OH)_2$. The hydrolysis step can include exposing the oxidized surface to moisture. This hydrolysis reaction can be done with steam at elevated temperature and pressure for a period of hours. For example, the temperature ranges can include 100 to 150 deg C., 150 to 250 deg C., or greater than 200 deg C. The pressure ranges can include 1 to 2 atm, 2 to 3 atm, or greater than 3 atm. It can also be done by exposing the scaffold to aqueous solution at neutral or basic pH.

Furthermore, a heat treatment step can be performed on the scaffold. The heat treatment step can be performed on the scaffold between the treatment that oxidizes the scaffold and the treatment converting the MgO to $Mg(OH)_2$. The heat treatment step consolidates and increases the density of the oxide layer, removes bound water, and thickens the oxide layer. The heat treatment step can be performed between the oxidation step and the hydrolysis step, after the hydrolysis step, or both. The heat treatment step may be performed by exposing the scaffold to high temperatures in a forced air convention oven, vacuum oven, or heated oven with inert atmosphere. The exposure temperature can be 40 to 340 deg C., 160 to 300 deg C., 80 to 25000 deg C., or 100 to 200 deg C.

In further embodiments, a magnesium or magnesium alloy scaffold includes a barrier layer of a water insoluble or very low water soluble magnesium salt on a surface of the scaffold. The layer may be over all or a portion of the scaffold. Exemplary magnesium salts include magnesium hydroxide ($Mg(OH)_2$), magnesium ammonium phosphate ($MgNH_4PO_4$), or magnesium phosphate ($Mg_3(PO_4)_2$). The solubility product constant for each of these salts is shown in Table 1.

TABLE 1

Magnesium salts for barrier layer.

| Magnesium Salt | Solubility Product Constant | Reagent Used to Make Salt |
|---|---|---|
| $Mg(OH)_2$ | $1.8 \times 10^{-11}$ | Water |
| $MgNH_4PO_4$ | $2.5 \times 10^{-13}$ | $NH_4H_2PO_4$, $NH_4^{4-}$ + $PO_4^{3-}$ + oxidizer |
| $Mg_3(PO_4)_2$ | $1 \times 10^{-25}$ | Phosphoric Acid ($H_3PO_4$), $PO_4^{3-}$ + oxidizer |

A very low solubility salt layer is preferred since it protects the scaffold from corrosion for a longer period of time. The slower the dissolution rate of the coating, the longer the corrosion of the scaffold is delayed. As shown in Table 1, $MgNH_4PO_4$ and $Mg_3(PO_4)_2$ have a much lower solubility than $Mg(OH)_2$. Salts which are less soluble than the naturally forming magnesium hydroxide are advantageous.

The magnesium salt layer can have a thickness of 0.1 to 10 microns, 0.1 to 5 microns, 1 to 5 microns, 2 to 3 microns, about 2 microns, or about 3 microns. The composition of the layer can be 100% of the magnesium salt. The composition of the layer can be 80 to 90 wt %, 90 to 95 wt %, or 95 to 99 wt % of the salt. The salt layer may be nonporous or have less than 1%, less than 2%, or less than 5% porosity. The salt layer may be drug-free.

The protective salt layer can be formed through precipitation of the magnesium salt on the surface of the magnesium or magnesium alloy scaffold. Coatings of these salts can be formed by exposing the magnesium alloy to dilute solutions of the acids listed in the table. In this case, the acid itself is the oxidizer, and hydrogen gas is formed by an oxidation-reduction reaction. Another approach is to expose the Mg alloy surface to phosphate or ammonium ions in an acidic solution where the low pH is not produced by phosphoric acid but by another mineral acid such as HCl or $H_2SO_4$. The pH should be low enough for the reaction to proceed, oxidizing some magnesium and forming the $MgNH_4PO_4$, or $Mg_3(PO_4)_2$ precipitate on the surface.

Another technique of making the coatings is to expose the Mg alloy surface to the necessary ions such as ammonium or phosphate in the presence of an oxidizer to oxidize the magnesium. In this case, the solution need not be at acidic pH with $H_3O^+$ as the oxidizer which is the situation when using dilute solutions of acids. The oxidizer may be dissolved oxygen, ozone, hydrogen peroxide, periodate, persulfate, permanganate, chromium oxide, perchlorate, chlorine, or hypochlorite.

Additionally, a heat treatment, as described above, may also be applied to the scaffold with the salt coating further solidifying the magnesium salt on the surface.

A drug or drugs can be mixed with the protection coating. The non-exclusive list of the drugs include those that have the properties of anti-proliferative agents, anti-inflammatory agents, antineoplastic agents, antiplatelet agents, anti-coagulant agents, anti-fibrin agents, antithrombonic agents, antimitotic agents, antibiotic agents, antiallergic agents, antioxidant agents as well as cystostatic agents. The coatings or scaffolds of the present invention can include any combination of the drugs or types of agents disclosed herein. The coatings or scaffolds of the present invention can exclude any combination of the drugs or types of agents disclosed herein.

Exemplary drugs include clobetasol, or derivatives and analogs, all taxoids such as taxols, docetaxel, and paclitaxel, paclitaxel derivatives, all mTOR binding drugs such as macrolide antibiotics, rapamycin, everolimus, structural derivatives and functional analogues of rapamycin, structural derivatives and functional analogues of everolimus, temsirolimus, deforolimus, myolimus, novolimus, FKBP-12 mediated mTOR inhibitors, biolimus, perfenidone, prodrugs thereof, co-drugs thereof, and combinations thereof. Representative rapamycin derivatives include 40-O-(3-hydroxy) propyl-rapamycin, 40-O-[2-(2-hydroxy)ethoxy]ethyl-rapamycin, or 40-O-tetrazole-rapamycin, 40-epi-(N-1-tetrazolyl)-rapamycin (ABT-578 manufactured by Abbott Laboratories, Abbott Park, Ill.), prodrugs thereof, co-drugs thereof, and combinations thereof.

Any of the above embodiments of scaffolds and scaffolds with protective or barrier coatings can further include a polymer coating over all or a portion of the surface of the scaffolds. The polymer of the polymer coating can be bioabsorbable. The polymer can be bulk eroding or surface eroding. The polymer can be an aliphatic polyester, such as a poly(L-lactide)-based polymer.

The coating can include a drug or drugs mixed, dispersed, or associated with the coating polymer. The polymer coating can have a thickness of 1 to 20 microns, less than 2 microns, less than 5 microns, 1 to 10 microns, 1 to 5 microns, 2 to 3 microns, about 2 microns, or about 3 microns.

Exemplary polymers for a polymer coating include poly(L-lactide), poly(D,L-lactide), poly(D-lactide), poly(D,L-lactide-co-glycolide), poly(D,L-lactide-co-L-lactide), poly(glycolide), poly(L-lactide-co-glycolide), poly(caprolactone), poly(L-lactide-co caprolactone), poly(D,L-lactide-co-caprolactone), and poly(glycolide-co-caprolactone). Other useful resorbable polymers include poly(ester-amide) copolymers, polycarbonate-ester copolymer such as poly(L-lactide-co-trimethylene carbonate), poly(orthoesters), poly(anhydrides), poly(4-hydroxybutyrate), poly(3-hydroxybutyrate), poly(4hydroxyvalerate), and poly(hydroxybutyrate-co-hydroxyvalerate).

In exemplary embodiments, magnesium can be alloyed with small of amounts of zinc, sodium, iron, potassium, calcium, aluminum, manganese, bismuth, silver, zirconium, thorium, yttrium, and rhenium. In some exemplary embodiments, the magnesium composition can be greater than 85%, 90%, 95%, or greater than 99% of the alloy. For example, AZ91 magnesium alloy includes magnesium (89.8%), aluminum (9%), zinc (2%), and manganese (0.2%). In other commercial embodiments, magnesium can be alloyed with lithium with a magnesium-lithium ratio in the range of 60:40. Other magnesium alloys include AM50A and AE42. Additionally, zinc can be alloyed with titanium (0.1-1%) to improve fracture toughness since zinc is a comparatively brittle material.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent comprising a scaffold composed entirely of a multiple phase alloy comprising a magnesium content of 30 to 80 wt % and a zinc content selected from the group consisting of 20 to 30 wt %, 30 to 40 wt %, 40 to 50 wt %, and 50 to 70 wt %.

2. The stent of claim 1, wherein the stent further includes a polymer coating over the scaffold.

3. The stent of claim 1, wherein the alloy comprises a magnesium content of 50 to 70 wt %.

4. The stent of claim 1, wherein the alloy is nonporous.

5. The stent of claim 1, wherein the alloy is porous.

6. The stent of claim 1, wherein the alloy is drug-free.

7. The stent of claim 1, wherein the zinc content is 20 to 30 wt %.

8. The stent of claim 1, wherein the multiple phase alloy includes a phase composed of magnesium.

9. The stent of claim 1, wherein the multiple phase alloy includes a phase composed of a magnesium alloy having up to 5 wt % of iron or zinc or 1 to 5 wt % of iron or zinc.

10. The stent of claim 1, wherein the multiple phase alloy includes a phase composed completely of zinc or iron.

* * * * *